United States Patent
Takahashi

(10) Patent No.: US 8,820,162 B2
(45) Date of Patent: Sep. 2, 2014

(54) PRESSED WORKPIECE INSPECTION APPARATUS

(75) Inventor: Kuniaki Takahashi, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 382 days.

(21) Appl. No.: 13/424,711

(22) Filed: Mar. 20, 2012

(65) Prior Publication Data

US 2012/0247208 A1 Oct. 4, 2012

(30) Foreign Application Priority Data

Mar. 30, 2011 (JP) ................................. 2011-076508

(51) Int. Cl.
| | | |
|---|---|---|
| G01N 29/04 | (2006.01) | |
| G01M 13/00 | (2006.01) | |
| G01M 7/00 | (2006.01) | |
| B25J 15/06 | (2006.01) | |
| G01N 29/14 | (2006.01) | |
| G01N 29/22 | (2006.01) | |

(52) U.S. Cl.
CPC ............. *G01N 29/225* (2013.01); *G01M 13/00* (2013.01); *G01M 7/00* (2013.01); *B25J 15/0616* (2013.01); *G01N 29/14* (2013.01); *G01N 29/043* (2013.01); *G01N 29/045* (2013.01); *Y10S 901/44* (2013.01)
USPC ............................................... 73/584; 901/44

(58) Field of Classification Search
USPC .............. 73/584, 862.041, 862.044, 862.625; 901/44
See application file for complete search history.

(56) References Cited

U.S. PATENT DOCUMENTS

| | | | | |
|---|---|---|---|---|
| 3,879,982 | A * | 4/1975 | Schmidt | 73/12.01 |
| 5,373,747 | A * | 12/1994 | Ogawa et al. | 73/862.581 |
| 7,258,379 | B2 * | 8/2007 | Ono et al. | 294/119.3 |
| 8,706,429 | B2 * | 4/2014 | Nakajima | 702/41 |
| 2012/0065902 | A1 * | 3/2012 | Nakajima | 702/41 |
| 2012/0290133 | A1 * | 11/2012 | Goto et al. | 700/258 |

FOREIGN PATENT DOCUMENTS

JP 2006-170684 A 6/2006

\* cited by examiner

*Primary Examiner* — J M Saint Surin
(74) *Attorney, Agent, or Firm* — McDermott Will & Emery LLP

(57) ABSTRACT

Provided is a pressed workpiece inspection apparatus. A main body of a finger mounted on a palletizer robot that transports a finished workpiece W to a palette includes the following components: two vacuum cups configured to attract the finished workpiece W, a vibrating mechanism configured to vibrate the finished workpiece W, a vibration detection sensor configured to detect a vibrational state of the finished workpiece W caused by the vibrating mechanism, a data logger configured to store and retain a detected signal from the vibration detection sensor, a transmitter configured to wirelessly transmit the detected signal stored and retained in the data logger to an analyzer, and a rechargeable battery configured to drive the vibration detection sensor, the data logger, and the transmitter. The analyzer determines whether or not the finished workpiece W is non-defective, based on the detected signal from the transmitter.

16 Claims, 8 Drawing Sheets

PRESSED WORKPIECE INSPECTION APPARATUS

CROSS-REFERENCE TO RELATED APPLICATIONS

The present application claims priority from Japanese Patent. Application No. 2011-076508 filed on Mar. 30, 2011, the entire contents of which are hereby incorporated by reference.

BACKGROUND OF THE INVENTION

1. Field of the Invention

The present invention relates to a pressed workpiece inspection apparatus that is provided in a press line particularly one including a destack feeder section, a press-molding section, and a palletizer section, and is configured to inspect whether or not a pressed workpiece is non-defective.

2. Description of the Related Art

Conventionally, the body of a vehicle or the like is formed by press-molding (plastic-molding) a plate material (work) such as steel or aluminum into the shape of a curved surface with intricate patterns of bulges and recesses by using a transfer press-molding machine, a tandem press-molding machine, or the like. Such a workpiece undergoes press-molding plural times by plural dies so as to be gradually formed into a final shape. Consequently, compared with the case where the final shape is formed by press-molding a single time, the molding process can be divided into sub-processes and thus a molding time can be reduced, thereby improving the overall production efficiency.

In the case where press-molding is performed plural times in this manner, press-molding is successively shifted (in approximately 3 seconds) from a current press-molding step to a subsequent press-molding step. Accordingly, it is difficult to arrange the timing of and a period of time for inspection of whether or not the pressed workpiece has a crack or the like. Thus, there has been a need to devise an inspection method and/or an inspection timing that can reduce the time taken to inspect whether or not the pressed workpiece is non-defective.

As an inspection apparatus that inspects whether or not the pressed workpiece is non-defective (or defective), for example, there is known a technology described in Japanese Unexamined Patent Application Publication (JP-A) No. 2006-170684 (FIGS. 1 and 2). The technology described in JP-A No. 2006-170684 (FIGS. 1 and 2) provides a mechanism including a transmission probe configured to generate ultrasonic waves, and a reception probe configured to receive the ultrasonic waves, these probes being moved over an object to be inspected (target pressed workpiece to be inspected). Each probe is moved back and forth over the object to be inspected at a predetermined scanning pitch, and subsequently, an image of the shape, size, or the like of a crack is captured using an infrared camera or a flash device, and then it is determined whether or not the object is non-defective, based on the captured data.

However, in the inspection apparatus described in the JP-A No. 2006-170684 (FIGS. 1 and 2) mentioned above, the inspection is performed using ultrasonic waves while each probe is moved back and forth over the object to be inspected at a predetermined scanning pitch, and subsequently, it is determined whether or not the object is non-defective, based on the resultant image captured by the infrared camera. Consequently, it takes a longer time for the determination, and furthermore, the inspection requires various pieces of equipment (each probe, a drive mechanism to move each probe, an infrared camera, a flash device, and the like). Thus, it is difficult to apply the inspection apparatus to a transfer press-molding machine or the like, and also the inspection apparatus tends to increase in size.

SUMMARY OF THE INVENTION

It is an object of the present invention to provide a pressed workpiece inspection apparatus that can inspect a pressed workpiece in a short time and enables equipment that is used for the inspection to be small.

A pressed workpiece inspection apparatus according to one aspect of the present invention determines whether or not a pressed workpiece is non-defective, and includes: a robot including a finger configured to hold the pressed workpiece, the robot being configured to transport the pressed workpiece. The finger has a vibrating mechanism configured to vibrate the pressed workpiece, a vibration detector configured to detect a vibrational state of the pressed workpiece caused by the vibrating mechanism, and a transmitter configured to transmit a detected signal from the vibration detector to an analyzer. The analyzer determines whether or not the pressed workpiece is non-defective, based on the detected signal from the transmitter.

According to the aspect, during a short period in which the pressed workpiece is transported, the analyzer can determine whether or not the pressed workpiece is non-defective, based on the detected signal regarding the defectiveness of the pressed workpiece. In addition, the equipment used for the inspection of the pressed workpiece can be implemented as small-sized equipment so as to be mounted on the finger, and thus the inspection apparatus can be small.

Preferably, the finger should include a rechargeable battery configured to supply power to at least one of the vibration detector and the transmitter, and should be taken out of or stored in a finger stocker by drive of the robot, the finger stocker being disposed in a movable range of the robot, and the finger stocker should have a charging device which charges the rechargeable battery.

Thus, by drive of the robot, the rechargeable battery can be automatically recharged and a finger can be replaced with another finger that has been recharged.

Preferably, the vibrating mechanism should be provided at a position that is substantially equidistant from a plurality of holding positions of the finger for the pressed workpiece.

Thus, the vibrating state of the pressed workpiece caused by the vibrating mechanism can be made favorable.

Preferably, the pressed workpiece inspection apparatus should further include an air source configured to drive a vacuum cup that is provided in the finger and attracts and holds the pressed workpiece. The air source drives the vibrating mechanism.

Accordingly, there is no need to separately provide a drive mechanism that drives the vibrating mechanism and the inspection apparatus can be simplified, thereby preventing the inspection apparatus from increasing in cost and size.

Preferably, the pressed workpiece inspection apparatus should further include a data logger configured to store and retain the detected signal from the vibration detector. The data logger is provided in the finger, and the transmitter wirelessly transmits the detected signal stored and retained in the data logger to the analyzer.

DESCRIPTION OF THE PREFERRED EMBODIMENTS

Hereinafter, a first embodiment of the present invention is described in detail with reference to the accompanying drawings.

Figure 1:
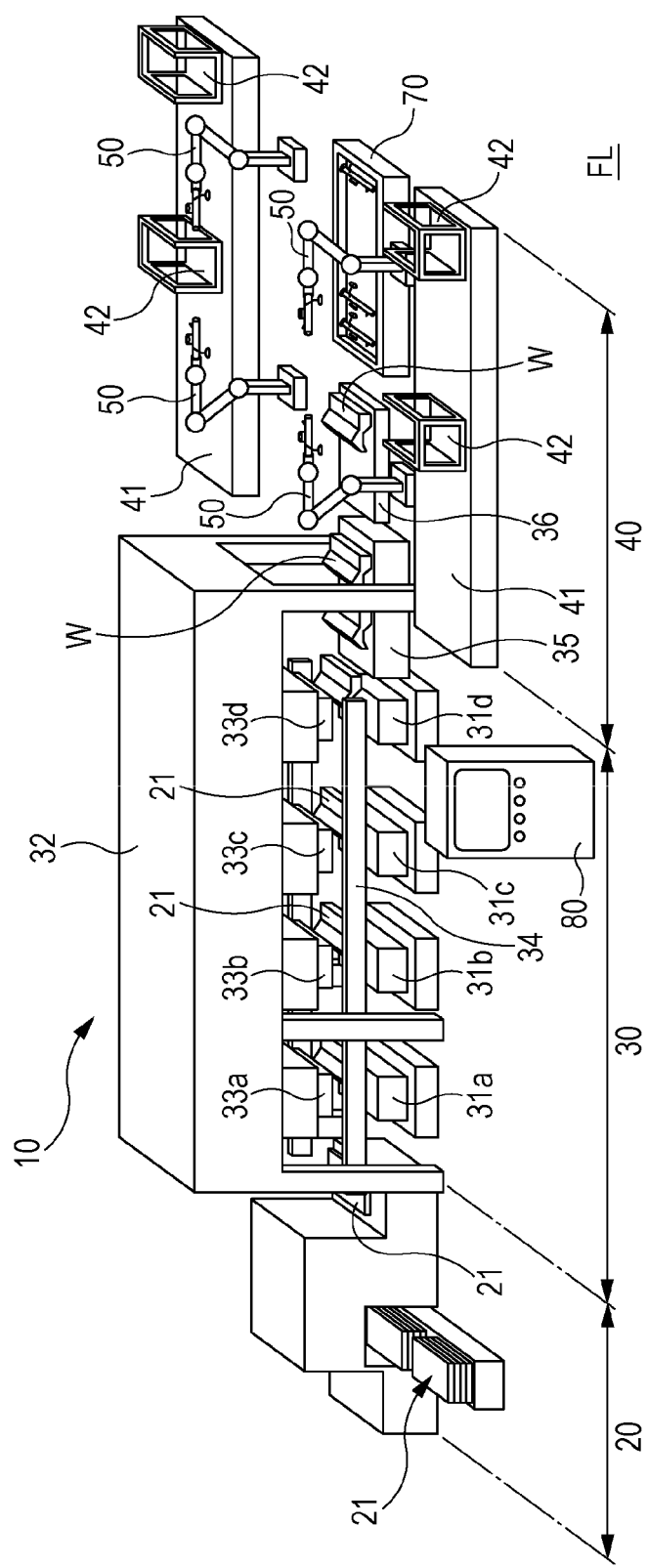
FIG. 1 is a perspective view of an exemplary press line.
Figure 2:
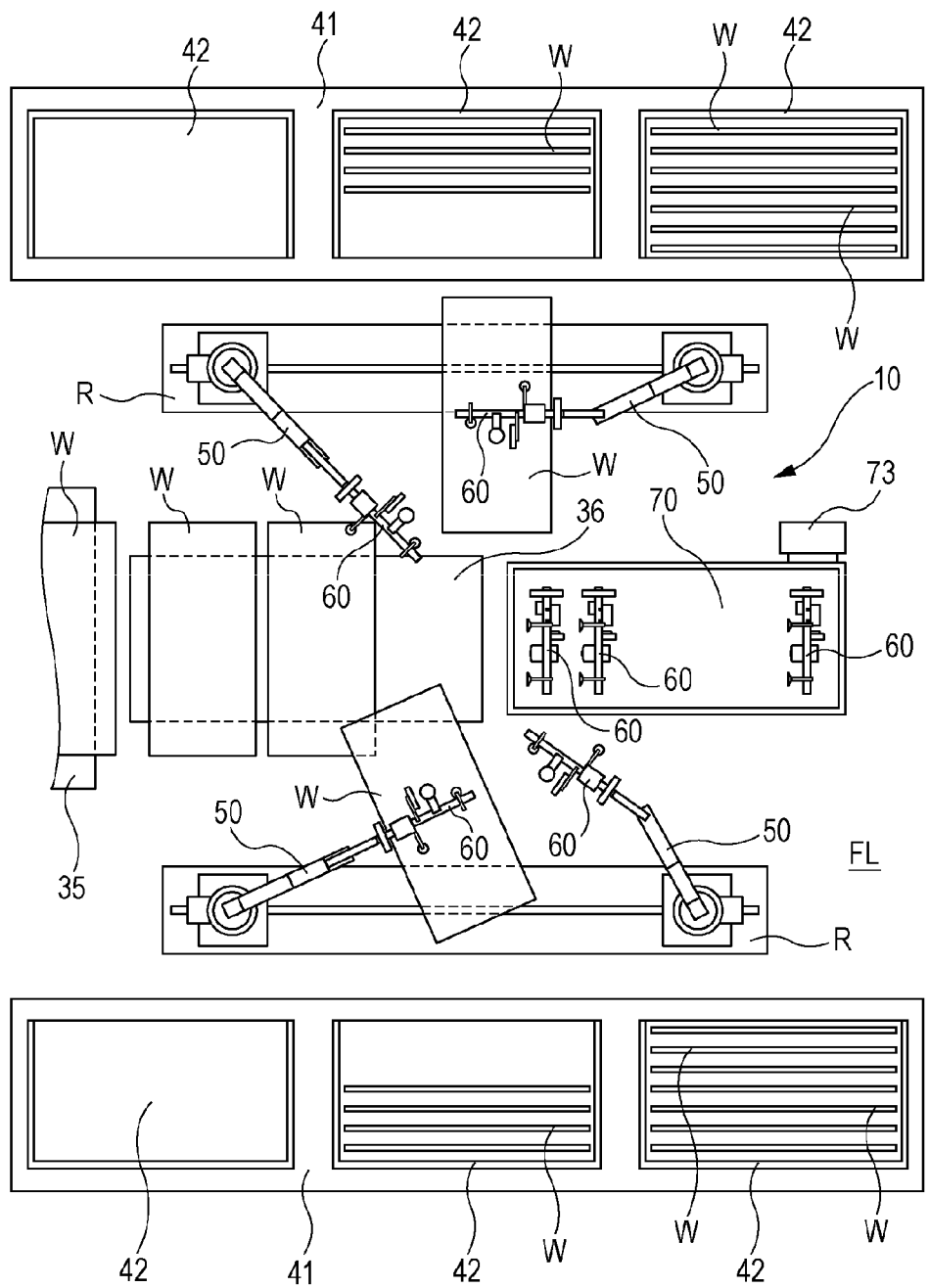
FIG. 2 is a top view of a palletizer section of FIG. 1.
Figure 3:
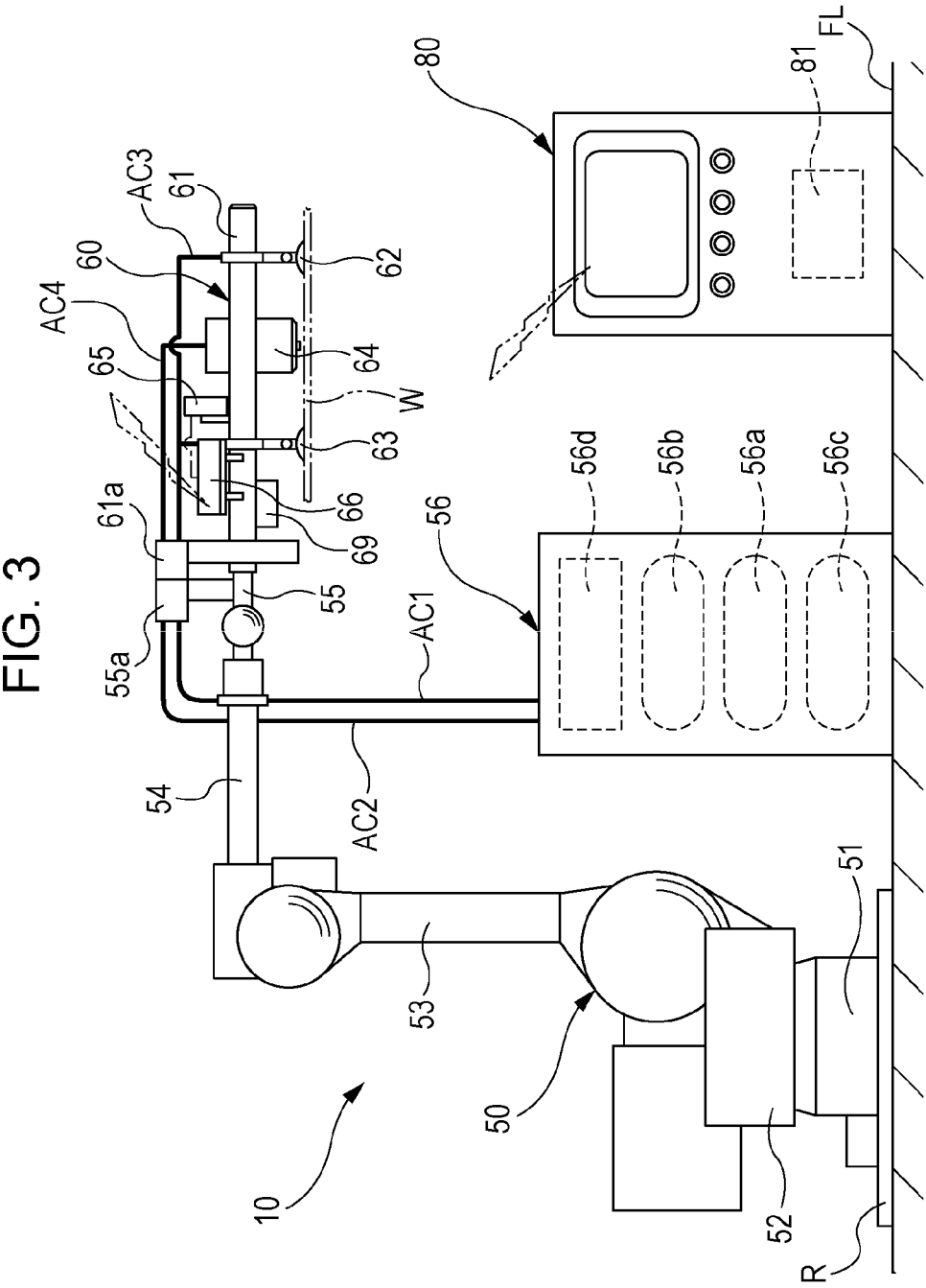
FIG. 3 illustrates the detailed structure of a palletizer robot.
Figure 4A:
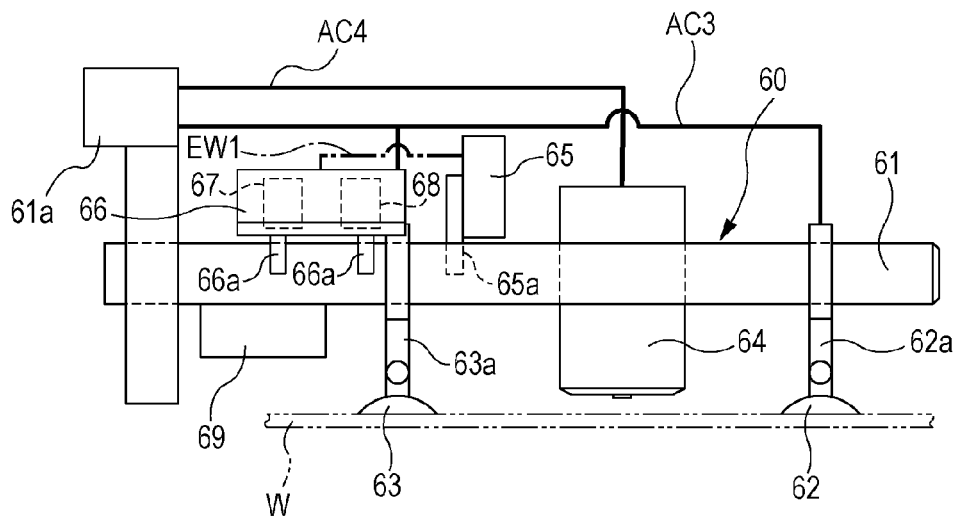
FIGS. 4A and 4B illustrate the detailed structure of a finger.
Figure 4B:
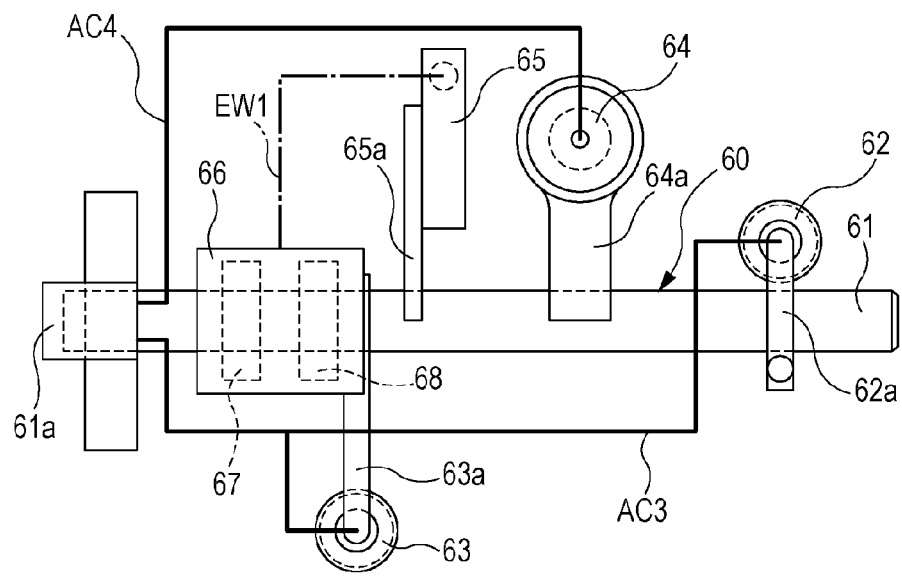
Figure 5:
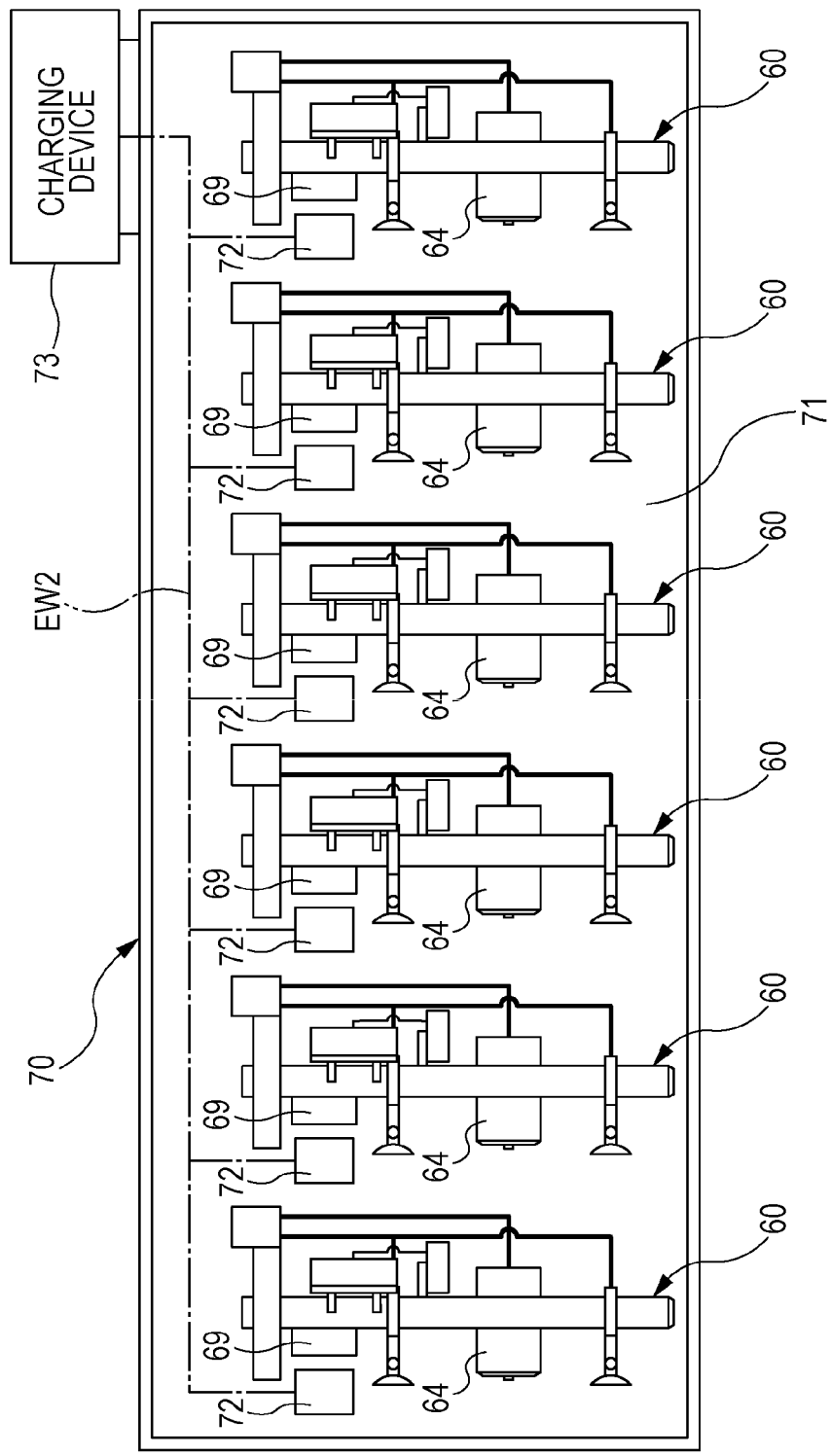
FIG. 5 illustrates a finger stocker in which fingers are stored.

FIG. 1 shows a perspective view of an exemplary press line; FIG. 2 shows a top view of a palletizer section of FIG. 1; FIG. 3 illustrates the detailed structure of a palletizer robot; FIGS. 4A and 4B illustrate the detailed structure of a finger; and FIG. 5 illustrates a finger stocker in which fingers are stored.

A transfer press lines 10 shown in FIG. 1 is provided as a plurality thereof side by side as press lines in rows inside a factory or the like in accordance with the shape of the pressed workpiece, and a destack feeder section 20 is disposed on the side (the left side of FIG. 1) to which pre-pressed steel sheets are supplied. In the destack feeder section 20, stacked steel sheets (work) 21 are separated sheet by sheet, and each separated steel sheet 21 is positioned for a subsequent press-molding section 30.

The press-molding section 30 forms a three-dimensional transfer press, and is configured to perform four pressing processes. Specifically, on a floor FL of a factory or the like, a first fixed die 31a, a second fixed die 31b, a third fixed die 31c, and a fourth fixed die 31d are disposed side by side in this order from the destack feeder section 20 at equal intervals. In addition, in a main body 32 of the press-molding section 30, a first vertically movable die 33a, a second vertically movable die 33b, a third vertically movable die 33c, and a fourth vertically movable die 33d are disposed side by side in this order at equal intervals so as to face the fixed dies 31a to 31d, respectively. Each of the vertically movable dies 33a to 33d is configured to be moved up or down at a predetermined timing (for example, every 3 seconds) by a link drive mechanism (not shown) that is provided inside the main body 32.

The fixed dies 31a to 31d and the vertically movable dies 33a to 33d are configured to gradually mold the steel sheet 21 into the final shape as the steel sheet 21 undergoes the process performed by the first dies 31a and 33a through to the process performed by the fourth dies 31d and 33d. Specifically, the steel sheet 21 undergoes the process performed by the first dies 31a and 33a through to the process performed by the fourth dies 31d and 33d so as to be gradually press-molded into the final shape.

In the press-molding section 30, there is provided a transport mechanism 34 for transporting the steel sheet 21 successively to the subsequent pressing process in synchronization with the up and down movement of each of the vertically movable dies 33a to 33d. Similarly to the vertically movable dies 33a to 33d, the transport mechanism 34 is driven at a predetermined timing (for example, every 3 seconds) by a link drive mechanism or the like which is provided inside the main body 32 so that the steel sheet 21 is transported.

In the proximity to the fourth dies 31d and 33d of the press-molding section 30, there is provided a workpiece-to-be-delivered storage 35, in which the steel sheet 21 that has undergone the four pressing processes (hereinafter referred to as a finished workpiece W) is stored. The finished workpiece W is stored in the workpiece-to-be-delivered storage 35 by driving of the transport mechanism 34. In the proximity so the workpiece-to-be-delivered storage 35, there is further provided a delivery conveyor 36, by which the finished workpiece W stored in the workpiece-to-be-delivered storage 35 is delivered to the subsequent process. The delivery conveyor 36 is provided in a movable range of each palletizer robot 50 so that the finished workpiece W on the delivery conveyor 36 can be easily taken out by each palletizer robot 50.

A palletizer section 40 ms disposed on the side so which the finished workpiece W from the press-molding section 30 is delivered (on the right side of FIG. 1), i.e., on the side of the delivery conveyor 36. In the palletizer section 40, a pair of pallet conveyors 41 that are spaced apart from each other in the transverse direction of the press-molding section 30 are provided, and each pallet conveyor 41 carries a plurality of palettes 42 to be loaded with the finished workpieces W.

As shown in FIG. 2 four palletizer robots (robots) 50 are disposed between the pallet conveyors 41. Specifically, two pairs of the palletizer robots 50 are disposed close to one of the pallet conveyors 41 and the other of the pallet conveyors 41, respectively. Each palletizer robot 50 moves along a rail R that is fixed to the floor FL, thereby allowing the palletizer robot 50 to move through a relatively wide range.

A finger stocker 70 is disposed in a movable range of each palletizer robot 50 between the pallet conveyors 41 of the palletizer section 40. A plurality of fingers 60 for each palletizer robot 50 are placed in the finger stocker 70, and each palletizer robot 50 is configured to store the finger 60 in or take out the finger 60 from the finger stocker 70 automatically at a predetermined timing.

As shown in FIG. 3, each palletizer robot 50 has a slide portion 51 chat is movably mounted on the rail R, and a main body 52 that is rotatably mounted on the slide portion 51. Furthermore, the base end of a first arm portion 53 is rotatably connected to the main body 52, and the base end of a second arm portion (arm) 54 is rotatably connected to the distal end of the first arm portion 53. In addition, the base end of an attachment socket portion 55 is rotatably connected to the distal end of the second arm portion 54, and the base end thereof is fixed.

The attachment socket portion 55 is provided with an air supply and exhaustion socket 55a, which is connected to a socket portion 61a that is provided on the side of the base end of a main body 61 of the finger 60. Here, as shown in FIGS. 1 and 3, each palletizer robot 50 is driven and controlled by a controller 80 provided in the proximity to the transfer press line 10.

An air supply and exhaustion mechanism 56 is secured to the floor FL, and is connected to the air supply and exhaustion socket 55a via a negative pressure air pipe AC1 and a positive pressure air pipe AC2. The air supply and exhaustion mechanism 56 includes a negative pressure air generator 56a configured to generate an air flow with a negative pressure, a high pressure air generator 56b configured to generate an air flow with a high pressure (positive pressure), a common air pump (air source) 56c configured to generate the air pressure of each of the air generators 56a and 56b, and a solenoid valve portion 56d configured to turn on/off an air flow from the air generators 56a and 56b to the respective air pipes AC1 and AC2. The air generators 56a and 56b, the air pump 56c, and the solenoid valve portion 56d are also driven and controlled by the controller 80.

The finger 60 shown in FIGS. 4A and 4B is attached to the distal end of the second arm portion 54 of the palletizer robot 50 via the attachment socket portion 55. The finger 60 is configured to hold she finished workpiece W that is a pressed product, and includes a rod-like main body 61 formed in a substantially cylindrical shape. According to the embodiment, the finger 60 has a configuration such that a vibrating mechanism 64, a vibration detection sensor 65, an electrical component box 66, and a rechargeable battery 69 are added to a finger that is generally used. Any of the vibrating mechanism 64, the vibration detection sensor 65, the electrical component box 66, and the charge battery 69 is a component that can be reduced in size, and thus the finger 60 is prevented from increasing in size.

The base end of the main body 61 is connected to the attachment socket portion 55, and is provided with the socket portion 61a that is connected to the air supply and exhaustion socket 55a. The distal end side and the base end side of the main body 61 in the longitudinal direction are provided with a first vacuum cup 62 and a second vacuum cup 63, respectively. The vacuum cups 62 and 63 are formed in a similar manner, and are configured to attract (hold) the finished workpiece W by supplying air with a negative pressure to each of the vacuum cups 62 and 63.

The vacuum cups 62 and 63 are supported by supporting legs 62a and 63a, respectively. As shown in FIG. 4B, the vacuum cups 62 and 63 are supported on opposite sides of the main body 61 by the supporting legs 62a and 63a, and are disposed at a predetermined interval in the longitudinal direction of the main body 61.

A negative pressure air pipe AC3 is provided between the vacuum cup 62 and the socket portion 61a, the vacuum cup 63 and the socket portion. 61a with the respective supporting legs 62a and 63a interposed therebetween. One end of the negative pressure air pipe AC3 is connected to the negative pressure air pipe AC1 via the socket portion 61a and the air supply and exhaustion socket 55a (see FIG. 3), and the other end of the negative pressure air pipe AC3 branches to the vacuum cups 62 and 63, then is connected to the respective supporting legs 62a and 63a. According to the embodiment, the supporting legs 62a and 63a have a hollow shape, and the hollows (not shown) of the supporting legs 62a and 63a communicate with she respective inner sides of the vacuum cups 62 and 63. That is, the vacuum cups 62 and 63 are connected to the negative pressure air generator 56a via the solenoid valve portion 56d of the air supply and exhaustion mechanism 56.

A vibrating mechanism. 64 for applying vibration at a predetermined position on the finished workpiece W held by each of the vacuum cups 62 and 63 is provided between the vacuum cups 62 and 63 in the longitudinal direction of the main body 61, on the first vacuum cup 62 side of the main body 61 in the transverse direction thereof. The vibrating mechanism 64 is provided at a position which is substantially equidistant from the vacuum cups 62 and 63, i.e., a position which is substantially equidistant from the holding positions of the finger 60 for the finished workpiece W, the vibrating mechanism 64 being firmly fixed to the main body 61 by a fixing leg 64a. The vibrating mechanism 64 is implemented as an air gun that discharges a pulse of air (not shown) by momentarily discharging high pressure air, thus vibration can be applied at a predetermined position on the finished workpiece W by continuously discharging a pulse of air from the vibrating mechanism 64 to the finished workpiece W.

One end of the positive pressure air pipe AC4 is connected to the vibrating mechanism 64. The other end of the positive pressure air pipe AC4 is connected to the positive pressure air pipe AC2 via the socket portion 61a and the air supply and exhaustion socket 55a (see FIG. 3). That is, the vibrating mechanism 64 is connected to the high pressure air generator 56b via the solenoid valve portion 56d of the air supply and exhaustion mechanism 56.

The vibration detection sensor (vibration detector) 65 is provided between the vibrating mechanism 64 and the second vacuum cup 63 in the longitudinal direction of the main body 61, on the vibrating mechanism 64 side of the main body 61 in the transverse direction thereof, and is configured to detect a vibrational state (displacement) of the finished workpiece W which has been vibrated (shaken) by the vibrating mechanism 64. The vibration detection sensor 65 is firmly fixed to the main body 61 by a fixing leg 65a. The vibration detection sensor 65 is configured to irradiate the finished workpiece W with an infrared laser while receiving a reflected laser thereof. In addition, the vibration detection sensor 65 is configured to detect a signal for the time between the irradiation of the infrared laser and the reception of the reflected laser, and to send the detected signal to a data logger 67 via electric wiring EW1.

According to the embodiment, the vibrating mechanism 64 and vibration detection sensor 65 are provided near the end of the second arm portion 54 of the palletizer robot 50. Consequently, the finished workpiece W and the vibration detection sensor 65 vibrate in synchronization with the vibration (noise) from the press-molding section 30 (see FIG. 1) or the like, thus undesired noise is relatively easy to cut out. Accordingly, the vibration detection sensor 65 can detect the vibrational state of the finished workpiece W with high accuracy. That is, the joint portion of the palletizer robot 50 or the like is configured to dampen the vibration received from the floor FL, which is caused by the press-molding section 30.

The electrical component box 66 is provided between the vibration detection sensor 65 and the socket portion 61a in the longitudinal direction of the main body 61. The electrical component box 66 is firmly fixed to the main body 61 by a pair of fixing legs 66a. The electrical component box 66 houses therein a data logger 67 configured to store and retain the detected signal (reflection time data of the laser) sent from the vibration detection sensor 65, and a transmitter 68 configured to wirelessly transmit (via wireless LAN) the detected signal stored and retained in the data logger 67 to an analyzer 81 provided in the controller 80 (see FIG. 3). The electrical component, box 66 further houses therein an electrical component such as a drive circuit (not shown) configured to drive the vibration detection sensor 65. In this manner, the detected signal is transmitted wirelessly, thereby eliminating troublesome wiring work, thus improving the work efficiency of a worker, while solving such a problem that a worker may trip over a wire.

The main body 61 is provided with the rechargeable battery 69 in close proximity to the electrical component box 66. The rechargeable battery 69 is formed, for example, of a secondary battery such as a lithium ion battery, and is configured to drive the vibration detection sensor 65, the data logger 67, and the transmitter 68 via the electrical component, i.e., the drive circuit provided within the electrical component box 66.

The controller 80 is provided with the analyzer 81 as shown in FIG. 3. The analyzer 81 is configured to determine whether or not the finished workpiece W has a defect such as a crack, i.e., whether or not the finished workpiece W is non-defective, based on the reflection time data of the laser, wirelessly transmitted from the transmitter 68 of the finger 60. Specifically, the analyzer 81 pre-stores the model data (ideal value) regarding the finished workpiece W, and compares the model data and the currently detected data.

In the case where the result of the comparison with the model data shows a significant difference, it is determined that the finished workpiece W is defective because of a possible crack or the like. On the other hand, in the case where the result of the comparison with the model data shows some difference, which is considered to be relatively small and within the range of an error, it is determined that the finished workpiece W is non-defective because of there being no cracks or the like.

In the present embodiment, a case is described where the single controller 80 controls the single transfer press line 10, however, the single controller 80 may collectively control a plurality of transfer press lines (not shown).

According so the embodiment, she pressed workpiece inspection apparatus includes the palletizer robot 50, she main body 61 of the finger 60, the vacuum cups 62 and 63, the vibrating mechanism 64, the vibration detection sensor 65, the data logger 67, the transmitter 68, the rechargeable battery 69, and the analyzer 81 of the controller 80.

As shown in FIG. 5, the finger stocker 70 includes a storage case 71 configured to store a plurality of fingers 60 (six fingers in FIG. 5), a plurality of dielectric chargers 72 provided in the storage case 71, corresponding to as many as fingers 60 that can be stored, and a charging device 73 provided outside the storage case 71 and electrically connected to each dielectric charger 72 via electric wiring EW2. In close proximity to each dielectric chargers 72, the corresponding rechargeable battery 69 of the finger 60 is disposed in a non-contact state so that the rechargeable battery 69 is charged via no electric wiring or the like.

Each palletizer robot 50 (see FIG. 2) is driven and controlled by the controller 80 so that a finger 60 that has already been charged is automatically taken from the finger stocker 70, or a finger 60, after being used, is stored in the finger stocker 70. According to the embodiment, there is no electric wire between each palletizer robot 50 and each finger 60 as well as between each finger 60 and the finger stocker 70. Consequently, each finger 60 can be easily replaced by driving and controlling the corresponding palletizer robot 50.

Figure 6:
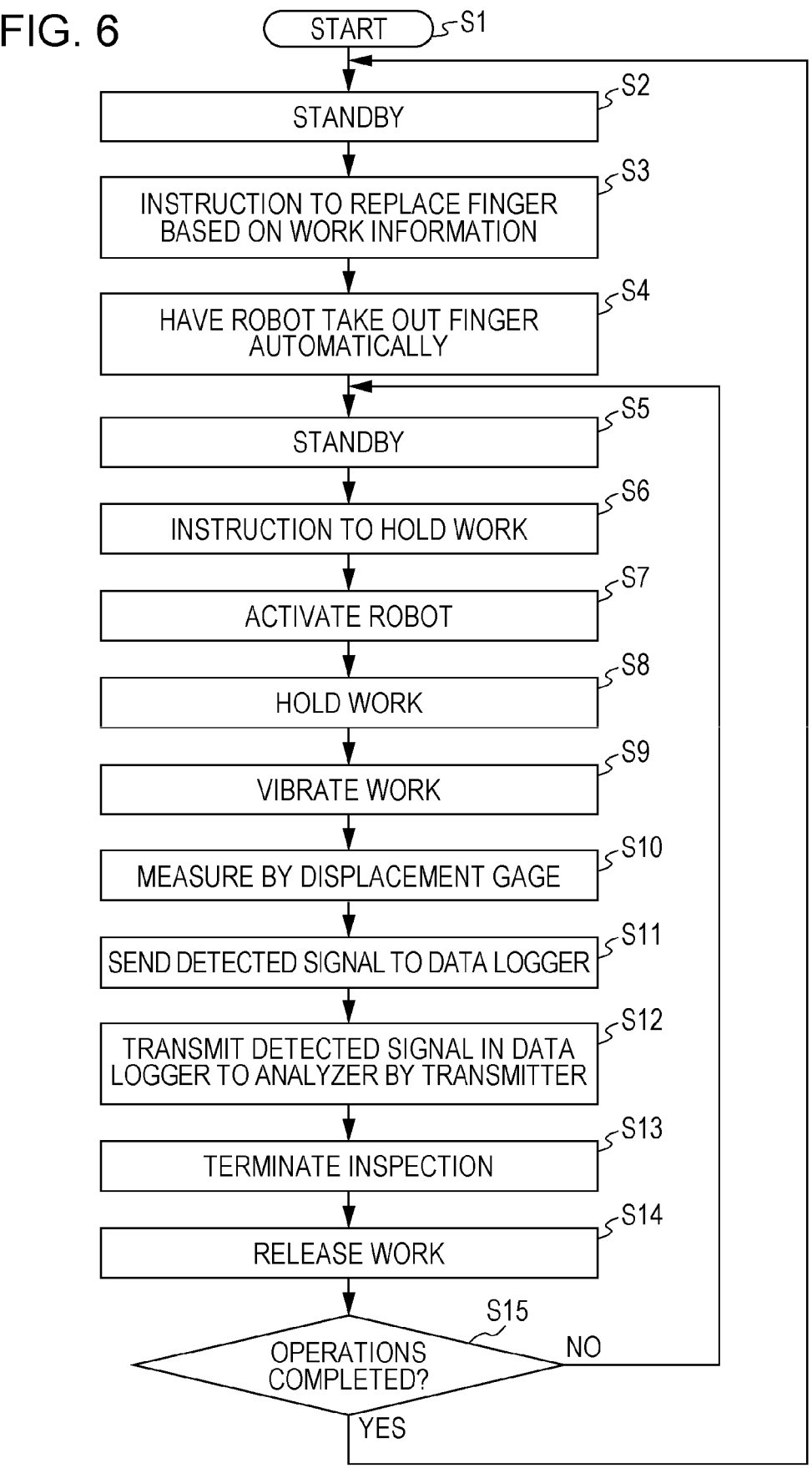
FIG. 6 is a flowchart illustrating an operation of a pressed workpiece inspection apparatus.

Next, the operation of the pressed workpiece inspection apparatus in the transfer press line 10 formed in the above manner is described in detail with reference to the accompanying drawings. FIG. 6 shows a flowchart illustrating the operation of the pressed workpiece inspection apparatus.

According to the embodiment of the invention, the pressed workpiece inspection apparatus is configured to determine whether or not the finished workpiece W is non-defective concurrently during a period (3 seconds or more) during which the finished workpiece W on the delivery conveyor 36 is transported to one of the palettes 42 in the palletizer section 40 shown in FIG. 1. That is, the period in which the finished workpiece W is transported from the delivery conveyor 36 to the palette 42 is effectively used.

As shown in FIG. 6, the operation of the pressed workpiece inspection apparatus starts when the system power of the transfer press line 10 is turned on in step S1. In step S2, the controller 80 (analyzer 81) is in a standby state. In subsequent step S3, information (work information) regarding the workpiece which is to be press-molded on the transfer press line 10 is inputted to the controller 80 by a keyboard input (not shown) from a worker or the like. Based on the information, an instruction of replacing the current finger is inputted to each palletizer robot 50. In this step, each palletizer robot 50 is driven and controlled so as to select one of the fingers 60 which can hold the finished workpiece W (see FIG. 2). By storing various fingers in the finger stocker 70, which are adapted to pressed workpieces of various shapes, each palletizer robot 50 can be driven and controlled in accordance with any of the pressed workpieces of various shapes.

In step S4, each of the palletizer robots 50 is driven and controlled by the controller 80 so that the finger 60 is automatically taken from the finger stocker 70. Here, each palletizer robot 50 automatically connects the air supply and exhaustion socket 55a to the socket portion 61a.

In step S5, each palletizer robot 50 is moved by the controller 80 to a reference position, for example, a position where the finished workpiece W on the delivery conveyor 36 can be quickly taken, then the palletizer robot 50 is set to be in a standby state. In subsequent step S6, which is triggered by the event, of the finished workpiece W being placed on the delivery conveyor 36, the controller 80 sends a command signal to one of the palletizer robots 50 to take (hold) the finished workpiece W.

In step S7, the palletizer robot 50 that has received the command signal is activated by the controller 80 so that the finger 60 is moved to the finished workpiece W on the delivery conveyor 36, then the vacuum cups 62 and 63 are pressed against respective predetermined positions on the finished workpiece W. In subsequent step S8, the solenoid valve portion 56d of the air supply and exhaustion mechanism 56 is controlled by the controller 80 so that each of the negative pressure air pipes AC1 and AC3 is caused to have a negative pressure by the negative pressure air generator 56a. Accordingly, the finished workpiece W is held by the vacuum cups 62 and 63.

The finished workpiece W held in step S8 is moved to one of the palettes 42 by the palletizer robot 50 being operated with the controller 80. Then, concurrently with the movement, the controller 80 controls the solenoid valve portion 56d of the air supply and exhaustion mechanism 56 so that each of the positive pressure air pipes AC2 and AC4 is caused to have momentarily a high pressure by the high pressure air generator 56b. Then, a pulse of air is discharged from the vibrating mechanism 64 so that a portion of the finished workpiece W directly below the vibrating mechanism 64 is vibrated (step S9). At this point, a pulse of air may be discharged once or plural times at a low frequency (5 to 6 Hz). In order to be different from noise (disturbance), however, a pulse of air is preferably discharged plural times regularly.

In step S10, the vibration detection sensor 65 is driven by the controller 80 to detect the displacement of a vibrating portion of the finished workpiece W. Subsequently, the signal (reflection time data of the laser) detected in step S10 is sent to the data logger 67 and is temporarily stored and retained therein (step S11). Subsequently, in step S12, the detected signal temporarily stored and retained in the data logger 67 is further wirelessly transmitted (via wireless LAN) from the transmitter 68 to the analyzer 81.

The analyzer 81 compares the model data and the currently detected data (detected signal), thereby determining whether or not the finished workpiece W is non-defective (determining whether or not the finished workpiece W has a crack), thus the inspection of the finished workpiece W is completed (step S13).

Subsequently, a finished workpiece W that is determined to be defective by the analyzer 81 is transported to the palette 42 for defective products (details are not shown) by driving and controlling the palletizer robot 50 with the controller 80. Subsequently, the solenoid valve portion 56d of the air supply and exhaustion mechanism 56 is controlled so as to stop the supply of negative pressure from the negative pressure air generator 56a to the negative pressure air pipes AC1 and AC3, thereby releasing the finished workpiece W that has been determined to be defective. On the other hand, a finished workpiece W that has been determined to be non-defective is transported to the palette 42 for non-defective products (details are not shown) by driving and controlling the palletizer robot 50 with the controller 80. Subsequently, the solenoid valve portion 56d of the air supply and exhaustion mechanism 56 is controlled so as to stop the supply of negative pressure from the negative pressure air generator 56a to the negative pressure air pipes AC1 and AC3, thereby releasing the finished workplace W that has been determined to be non-defective (step S14).

In subsequent step S15, it is determined whether or not a series of operations to be performed by the transfer press line 10 have been completed. When the press-molding is not yet completed (determination of "no"), the process returns to step S5, and the palletizer robot 50 is set to be in a standby state to prepare for the transport and inspection of a subsequent finished workpiece W. On the other hand, when the series of operations have been completed (determination of "yes"), the process returns to step S2, and the controller 80 (the palletizer robot 50) is set to be in a standby state to wait for an input of work information for another shape to be press-molded subsequently.

As described in detail above, in she pressed workpiece inspection apparatus according to the first embodiment, the main body 61 of the finger 60 mounted on the palletizer robot 50 which transports the finished workpiece W to the palette 42 includes the following attachments: the vacuum cups 62 and 63 configured to attract the finished workpiece W, the vibrating mechanism 64 configured to vibrate the finished workpiece W, the vibration detection sensor 65 configured to detect the vibrational state of the finished workpiece W caused by the vibrating mechanism 64, the data logger 67 configured to store and retain the detected signal from the vibration detection sensor 65, the transmitter 68 configured to wirelessly transmit the detected signal stored and retained in the data logger 67 to the analyzer 81, and the rechargeable battery 69 configured to drive the vibration detection sensor 65, the data logger 67, and the transmitter 68. The analyzer 81 determines whether or not the finished workpiece W is non-defective, based on the detected signal from the transmitter 68.

Consequently, during a short period during which the finished workpiece W is transported to the palette 42, the analyzer 81 can determine whether or not the finished workpiece W is non-defective, based on the detected signal regarding the defectiveness of the finished workpiece W. In addition, the equipment (such as the vibrating mechanism 64) used for the inspection of the finished workpiece W can be implemented as small-sized equipment which can be mounted on the finger 60, thus the inspection apparatus can be small in size.

In addition, in the pressed workpiece inspection apparatus according to the first embodiment, the finger 60 is taken out of or stored in the finger stocker 70 by driving the palletizer robot 50, the finger stocker 70 being disposed in a movable range of the palletizer robot 50, and the finger stocker 70 has the charging device 73 which charges the rechargeable battery 69. Thus, by driving the palletizer robot 50, the rechargeable battery 69 can be automatically recharged and a finger can be replaced with a finger 60 that has been recharged.

In the pressed workpiece inspection apparatus according to the first embodiment, the vibrating mechanism 64 is provided at a position that is substantially equidistant from the vacuum cups 62 and 63, thus, the vibrating state of the finished workpiece W caused by the vibrating mechanism 64 can be made favorable. That, the vibration amplitude is increased so that vibration can be easily detected by the vibration detection sensor 65, shuts eventually, the accuracy in determining whether or not the finished workpiece W is non-defective can be improved.

In addition, according to the pressed workpiece inspection apparatus of the firs embodiment, the vibrating mechanism 64 is driven by the air pump 56c that drives the vacuum cups 62 and 63, and thus a drive mechanism for driving the vibrating mechanism 64 is not required to be separately provided. Accordingly, the inspection apparatus can be simplified, thereby preventing the inspection apparatus from increasing in cost and size.

Next, a second embodiment of the present invention is described in detail with reference to the accompanying drawings. The components in the second embodiment, having similar functions to those in the first embodiment described above are labeled with the same reference symbols, and the description of the components is omitted.

Figure 7:
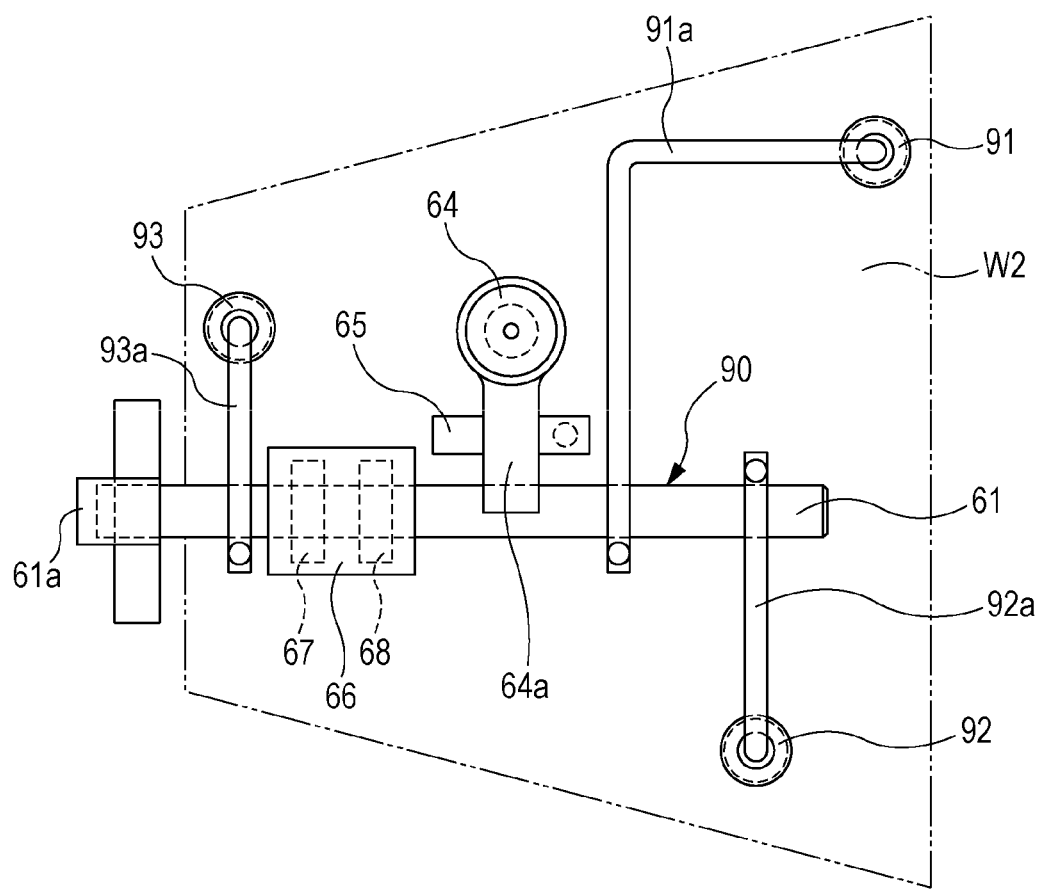
FIG. 7 illustrates a finger according to a second embodiment.

FIG. 7 is an illustration of a finger according to the second embodiment. In the second embodiment, the finger differs from that in the first embodiment described above only in terms of its shape.

As shown in FIG. 7, a finger 90 according to the second embodiment is provided for holding a finished workpiece W2 in which the base end side of the main body 61 is narrower and the distal end side of the main body 61 is wider. The finger 90 includes a first vacuum cup 91, a second vacuum cup 92, and a third vacuum cup 93 in this order from the distal end side of the main body 61 so as to hold the finished workpiece W2 at three points.

The first vacuum cup 91 and the second vacuum cup 92 are disposed at substantially the same position in the longitudinal direction of the main body 61, and oppose each other across the main body 61. A supporting leg 91a of the first vacuum cup 91 is formed in a substantially L-like shape, and a supporting leg 92a of the second vacuum cup 92 is formed in a linear shape. The third vacuum cup 93 is disposed on the first vacuum cup 91 side of the main body 61 in the transverse direction thereof, and a supporting leg 93a is formed in a linear shape.

The vibrating mechanism 64 is disposed between the first vacuum cup 91 and the third vacuum cup 93, at a position that is substantially equidistant from the vacuum cups 91, 92, and 93. The vibration detection sensor 65 is fixed to the fixing leg 64a of the vibrating mechanism 64 so as to cross the fixing leg 64a, and thus the vibration detection sensor 65 is disposed in closer proximity to the vibrating mechanism 64. Consequently, the detection accuracy of the vibration detection sensor 65 is further improved.

Also in the second embodiment formed in the above manner, an operational effect similar to that in the first embodiment described above can be achieved.

Next, a third embodiment of the present invention is described in detail with reference to the accompanying drawings. The components in the third embodiment, having similar functions to those in the first embodiment described above are labeled with the same reference symbols, and the description of the components is omitted.

Figure 8:
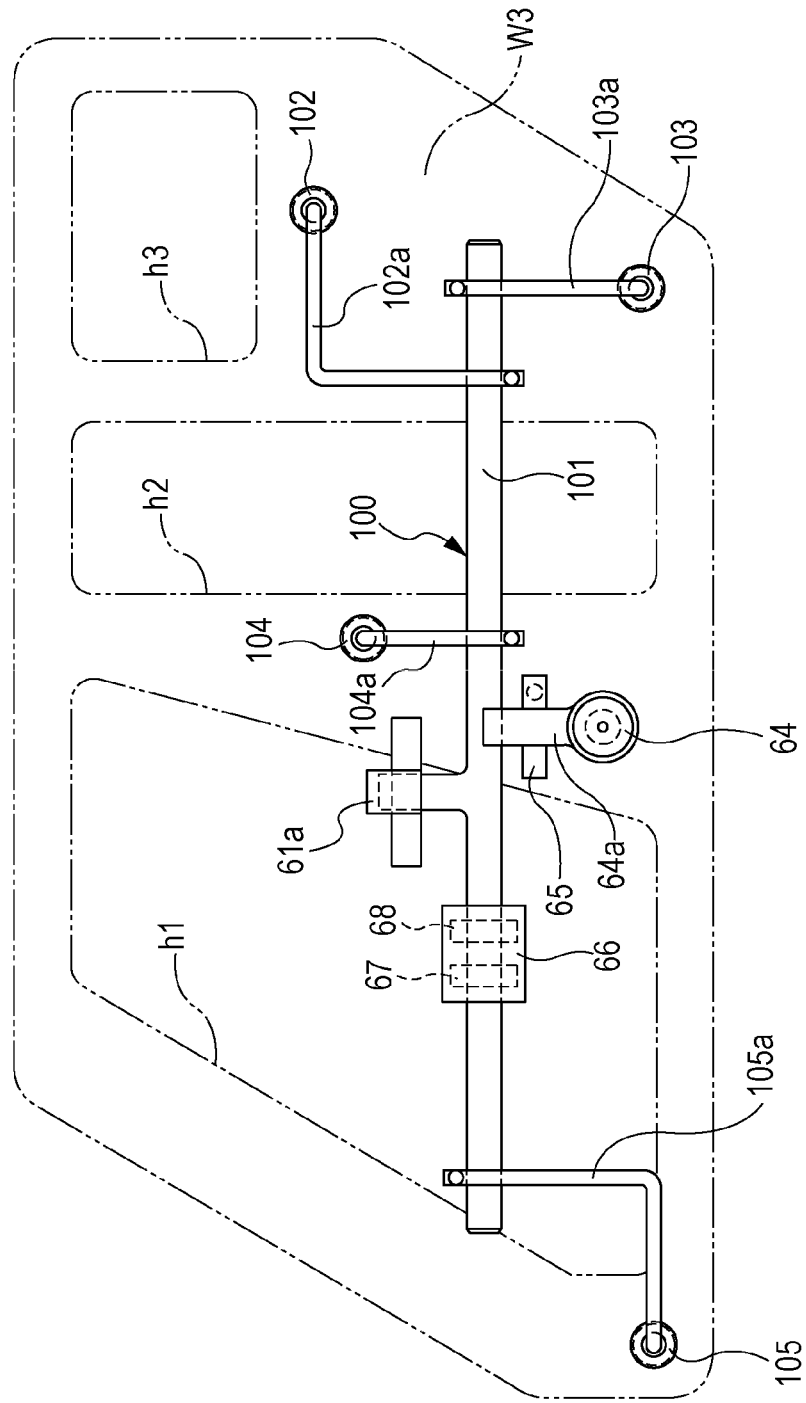
FIG. 8 illustrates a finger according to a third embodiment.

FIG. 8 is an illustration of a finger according to the third embodiment. In the third embodiment, the finger differs from that in the first embodiment described above only in terms of its shape.

As shown in FIG. 8, a finger 100 according to the third embodiment is provided for holding an intricately shaped finished workpiece W3 having a plurality of punched portions h1, h2, and h3. The finger 100 includes a substantially T-shaped main body 101, and the socket portion 61a is provided in substantially the middle of the main body 101. On one side (the right side of FIG. 8) of the main body 101 with respect to the socket part 61a, there are provided a first vacuum cup 102, a second vacuum cup 103, and a third vacuum cup 104 in this order from the distal end. On the other hand, on the other side (the left side of FIG. 8) of the main body 101 with respect to the socket part 61*a*, a fourth vacuum cup 105 is provided at the end. That is, the finger 100 is configured to hold the finished workpiece W3 with four points thereon different from the punched portions h1, h2, and h3.

The first vacuum cup 102 and the second vacuum cup 103 are disposed at substantially the same position in the longitudinal direction of the main body 101, and oppose each other across the main body 101. A supporting leg 102*a* of the first vacuum cup 102 is formed in a substantially L-like shape, and a supporting leg 103*a* of the second vacuum cup 103 is formed in a linear shape. In addition, the third vacuum cup 104 is disposed on the first vacuum cup 102 side of the main body 101 in the transverse direction thereof, and a supporting leg 104*a* is formed in a linear shape. In addition, the fourth vacuum cup 105 is disposed on the second vacuum cup 103 side of the main body 101 in the transverse direction thereof, and a supporting leg 105*a* is formed in a substantially L-like shape.

The vibrating mechanism 64 is disposed in close proximity to the socket portion 61*a* between the second vacuum cup 103 and the fourth vacuum cup 105, at a position that is substantially equidistant from the vacuum cups 102 and 103, and 105 excluding the third vacuum cup 104. The vibration detection sensor 65 is fixed to the fixing leg 64*a* of the vibrating mechanism 64 so as to cross the fixing leg 64*a*, thus the vibration detection sensor 65 is disposed in closer proximity to the vibrating mechanism 64. Consequently, the detection accuracy of the vibration detection sensor 65 is further improved.

Also in the third embodiment formed in the above manner, an operational effect similar to that in the first embodiment described above can be achieved.

The present invention is not limited to the above-described embodiments, and it is needless to state that various modifications can be made in a range not departing from the spirit of the invention. For example, in each of the above-described embodiments, a case has been described where the non-contact vibration detection sensor 65 that emits an infrared laser and receives a reflected laser is used as a vibration detector. However, the present invention is not limited to this case, and a contact acceleration sensor or the like having a movable portion may be employed. Alternatively, as a non-contact vibration detector, a microphone or the like which detects the sound waves generated at a vibrating portion can be used. In essence, as long as a vibration detector can detect a vibrational state at a vibrating portion, a vibration detector can be employed regardless of whether it is of a non-contact type or a contact type.

What is claimed is:

1. A pressed workpiece inspection apparatus that determines whether or not a pressed workpiece is non-defective, the pressed workpiece inspection apparatus comprising:
   a robot including a finger configured to hold the pressed workpiece, the robot being configured to transport the pressed workpiece,
   wherein the finger has
   a vibrating mechanism configured to vibrate the pressed workpiece,
   a vibration detector configured to detect a vibrational state of the pressed workpiece caused by the vibrating mechanism, and
   a transmitter configured so transmit a detected signal from the vibration detector to an analyzer, and
   wherein the analyzer determines whether or not the pressed workpiece is non-defective, based on the detected signal from the transmitter.

2. The pressed workpiece inspection apparatus according to claim 1,
   wherein the finger includes a rechargeable battery configured to supply power to at least one of the vibration detector and the transmitter, and is taken out of or stored in a finger stocker by drive of the robot, the finger stocker being disposed in a movable range of the robot, and the finger stocker has a charging device which charges the rechargeable battery.

3. The pressed workpiece inspection apparatus according to claim 2,
   wherein the vibrating mechanism is provided at a position that is substantially equidistant from a plurality of holding positions of the finger for the pressed workpiece.

4. The pressed workpiece inspection apparatus according to claim 3, further comprising:
   an air source configured to drive a vacuum cup that is provided in the finger and attracts and holds the pressed workpiece, wherein the air source drives the vibrating mechanism.

5. The pressed workpiece inspection apparatus according to claim 4, further comprising:
   a data logger configured to store and retain the detected signal from the vibration detector, wherein the data logger is provided in the finger, and the transmitter wirelessly transmits the detected signal stored and retained in the data logger to the analyzer.

6. The pressed workpiece inspection apparatus according to claim 3, further comprising:
   a data logger configured to store and retain the detected signal from the vibration detector, wherein the data logger is provided in the finger, and the transmitter wirelessly transmits the detected signal stored and retained in the data logger to the analyzer.

7. The pressed workpiece inspection apparatus according to claim 2, further comprising:
   an air source configured to drive a vacuum cup that is provided in the finger and attracts and holds the pressed workpiece, wherein the air source drives the vibrating mechanism.

8. The pressed workpiece inspection apparatus according to claim 7, further comprising:
   a data logger configured to store and retain the detected signal from the vibration detector, wherein the data logger is provided in the finger, and the transmitter wirelessly transmits the detected signal stored and retained in the data logger to the analyzer.

9. The pressed workpiece inspection apparatus according to claim 2, further comprising:
   a data logger configured to store and retain the detected signal from the vibration detector, wherein the data logger is provided in the finger, and the transmitter wirelessly transmits the detected signal stored and retained in the data logger to the analyzer.

10. The pressed workpiece inspection apparatus according to claim 1,
    wherein the vibrating mechanism is provided at a position that is substantially equidistant from a plurality of holding positions of the finger for the pressed workpiece.

11. The pressed workpiece inspection apparatus according to claim 10, further comprising:

an air source configured to drive a vacuum cup that is provided in the finger and attracts and holds the pressed workpiece, wherein the air source drives the vibrating mechanism.

12. The pressed workpiece inspection apparatus according to claim 11, further comprising:
a data logger configured to store and retain the detected signal from the vibration detector, wherein the data logger is provided in the finger, and the transmitter wirelessly transmits the detected signal stored and retained in the data logger to the analyzer.

13. The pressed workpiece inspection apparatus according to claim 10, further comprising:
a data logger configured to store and retain the detected signal from the vibration detector, wherein the data logger is provided in the finger, and the transmitter wirelessly transmits the detected signal stored and retained in the data logger to the analyzer.

14. The pressed workpiece inspection apparatus according to claim 1, further comprising:
an air source configured to drive a vacuum cup that is provided in the finger and attracts and holds the pressed workpiece, wherein the air source drives the vibrating mechanism.

15. The pressed workpiece inspection apparatus according to claim 14, further comprising:
a data logger configured to store and retain the detected signal from the vibration detector, wherein the data logger is provided in the finger, and the transmitter wirelessly transmits the detected signal stored and retained in the data logger to the analyzer.

16. The pressed workpiece inspection apparatus according to claim 1, further comprising:
a data logger configured to store and retain the detected signal from the vibration detector, wherein the data logger is provided in the finger, and the transmitter wirelessly transmits the detected signal stored and retained in the data logger to the analyzer.

* * * * *